United States Patent [19]

Skubick

[11] Patent Number: 5,662,118
[45] Date of Patent: Sep. 2, 1997

[54] SYSTEM FOR DIAGNOSING MUSCULOSKELETAL DISORDERS

[76] Inventor: Daniel Lewis Skubick, 1413 Sumneytown Pike, Ambler, Pa. 19002

[21] Appl. No.: 456,601

[22] Filed: Jun. 1, 1995

[51] Int. Cl.$^6$ ........................................... A61B 7/00
[52] U.S. Cl. ................................................ 128/733
[58] Field of Search ................................ 128/733

[56] References Cited

U.S. PATENT DOCUMENTS

| | | | |
|---|---|---|---|
| 3,905,355 | 9/1975 | Brudny | 128/2.1 M |
| 4,148,303 | 4/1979 | Cohen | 128/733 |
| 4,213,466 | 7/1980 | Stulen | 128/733 |
| 4,213,467 | 7/1980 | Stulen et al. | 128/733 |
| 4,448,203 | 5/1984 | Williamson et al. | 128/733 |
| 5,163,440 | 11/1992 | DeLuca et al. | 128/733 |
| 5,277,197 | 1/1994 | Church et al. | 128/733 |
| 5,318,039 | 6/1994 | Kadefors et al. | 128/733 |

*Primary Examiner*—Vincent Millin
*Assistant Examiner*—Robert N. Wieland
*Attorney, Agent, or Firm*—Panitch Schwarze Jacobs & Nadel, P.C.

[57] ABSTRACT

A system for identifying muscular abnormalities in a human patient and diagnosing musculoskeletal disorders from the abnormalities includes collecting electromyographic signals from selected muscles of the patient while the patient undergoes a plurality of protocols, creating muscle activity samples from the electromyographic signals collected from the patient, defining one of more indices by algebraically combining selected muscle activity samples, calculating the index of the patient from the selected group of collected samples, and comparing the index to a normative range of values for the index to determine whether the patient has a muscular abnormality and to diagnose the abnormality. The system is employed to identify dysfunctional psychophysiological and biomechanical muscle patterns in the upper quarter and forearm of the patient.

22 Claims, 11 Drawing Sheets

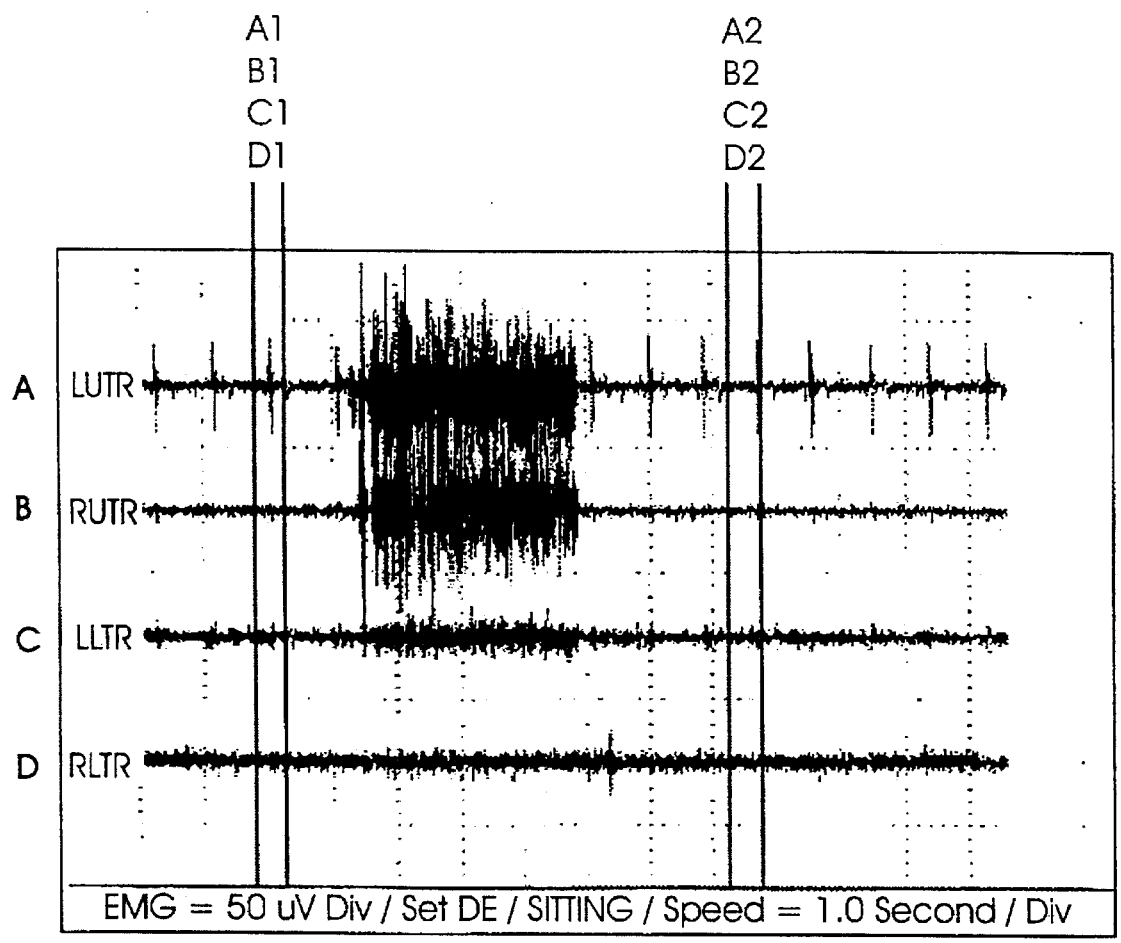
A1= 3.9  A2= 3.8
B1= 3.5  B2= 3.4
C1= 4.1  C2= 4.2
D1= 3.9  D2= 4.1
Fig. 3A   Protocol 1

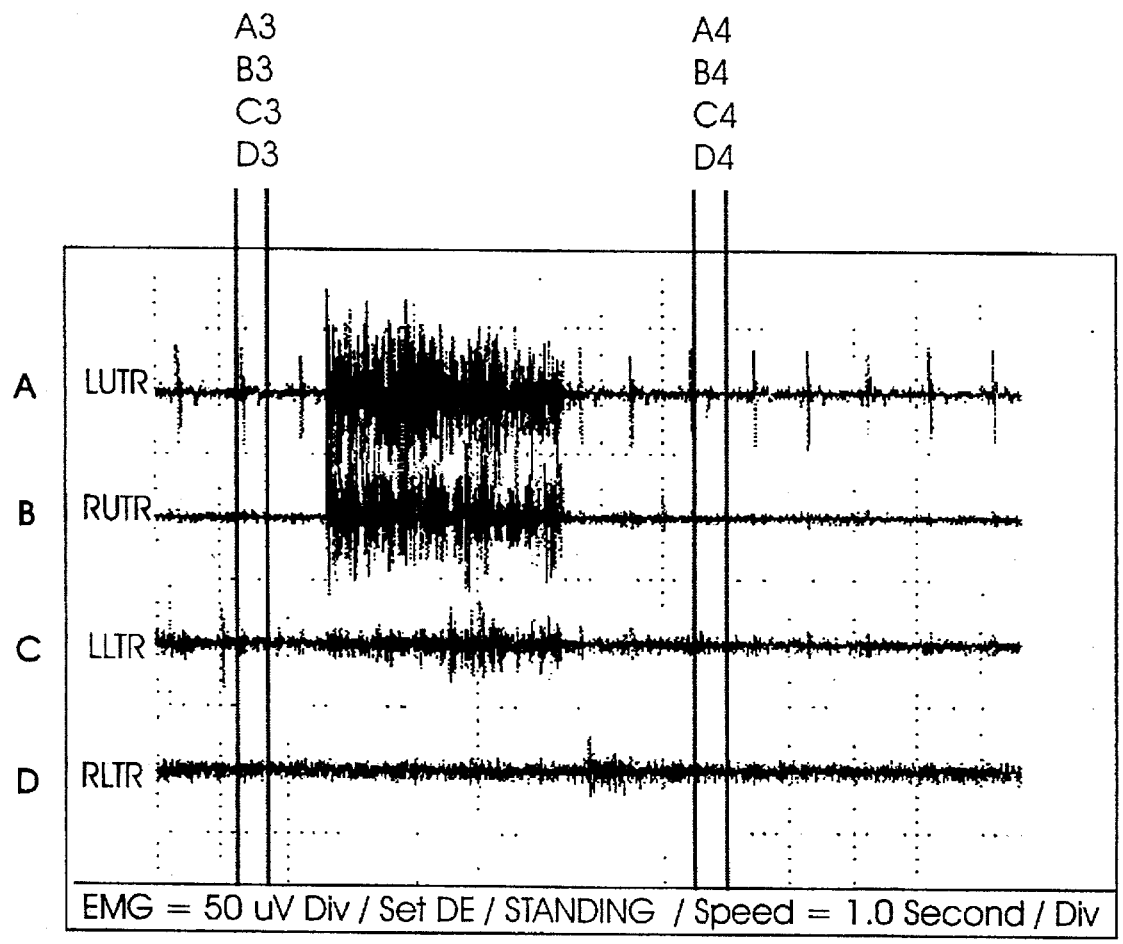
Fig. 3B  Protocol 2

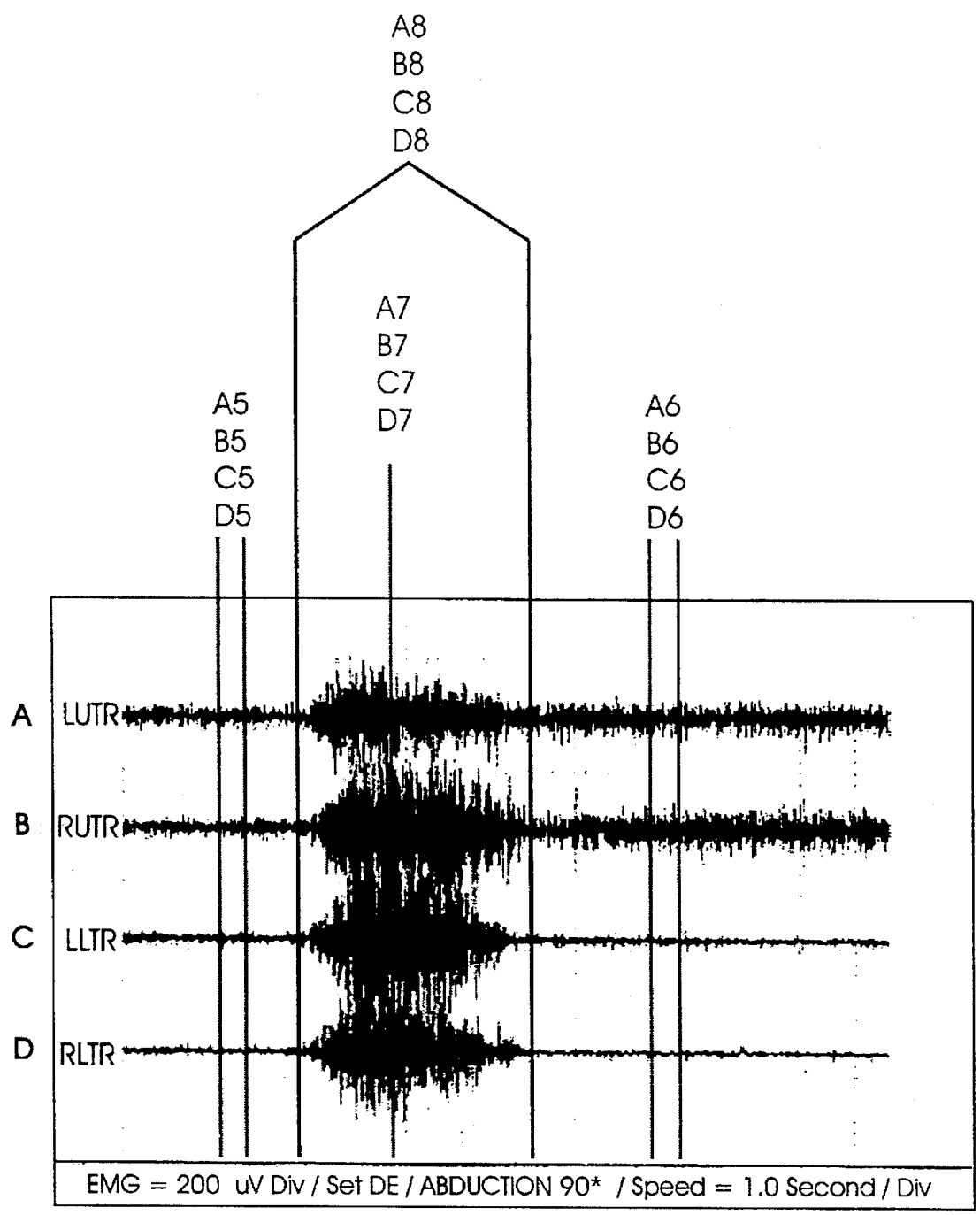
Fig. 3C   Protocol 3

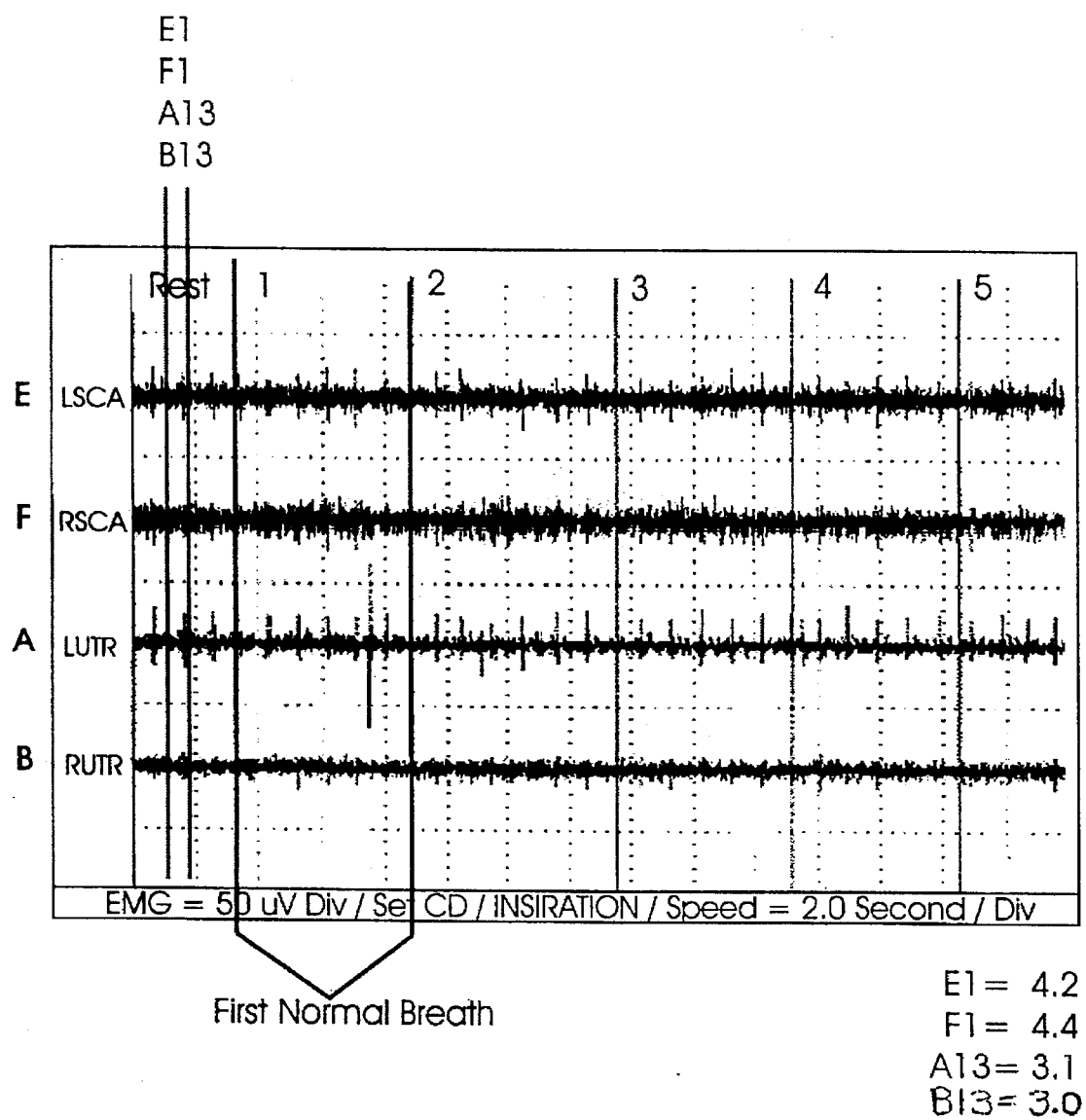
Fig. 3D Protocol 5

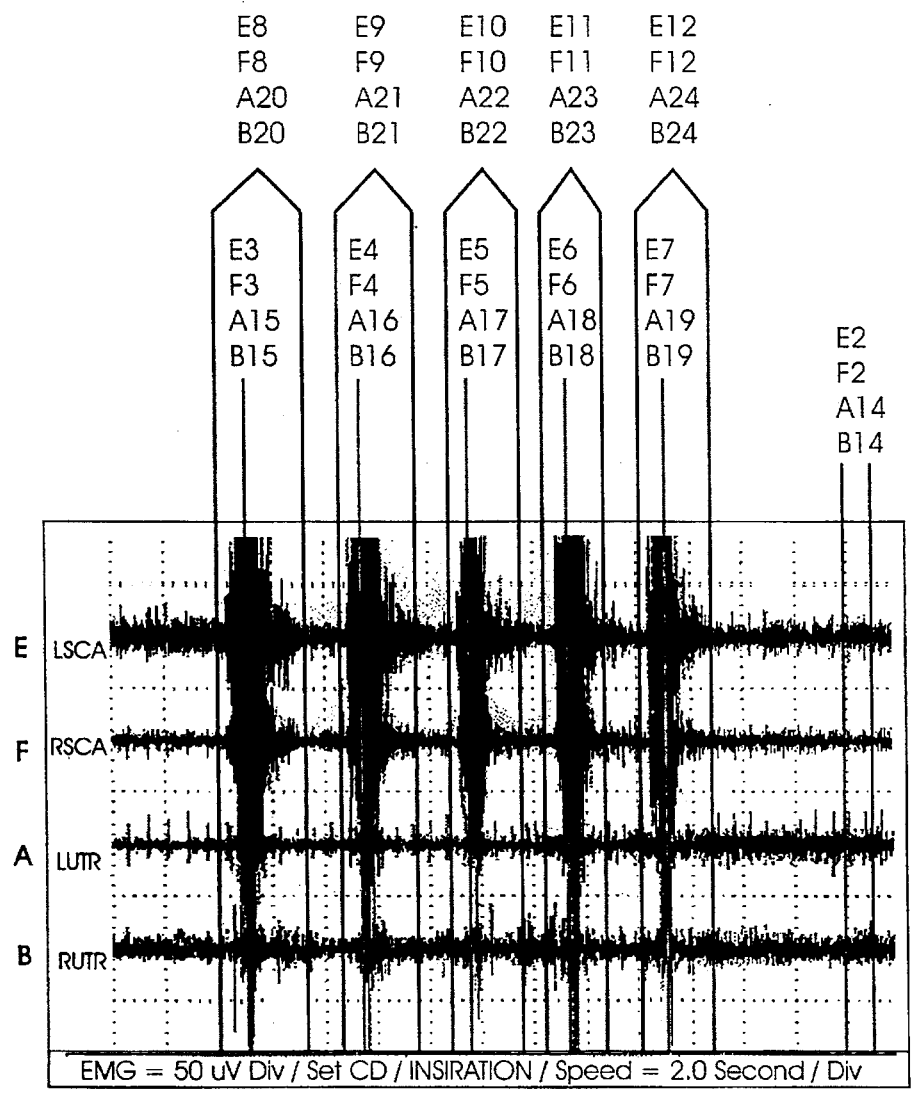
Fig. 3E  Protocol 5

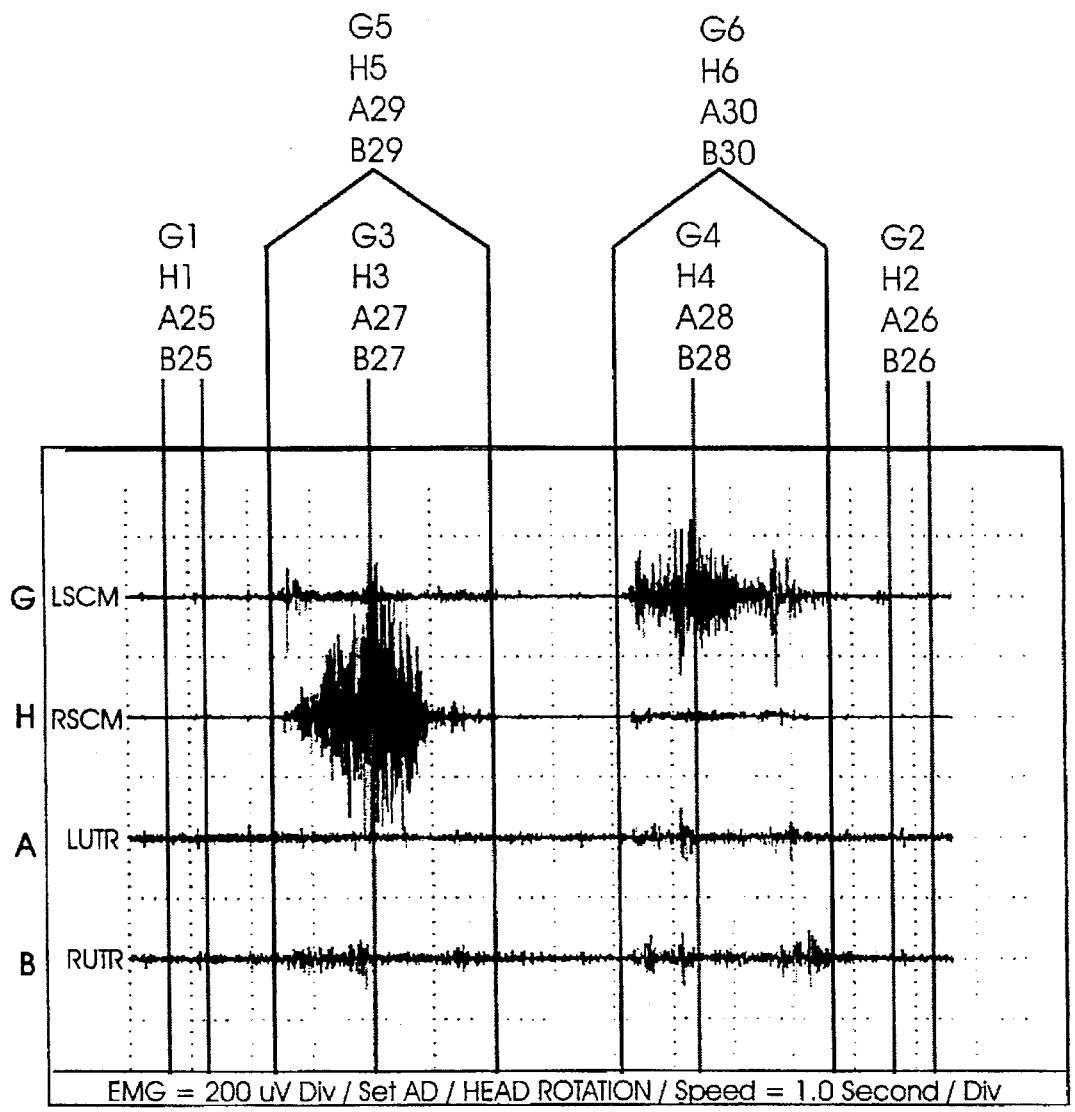
Fig. 3F Protocol 6

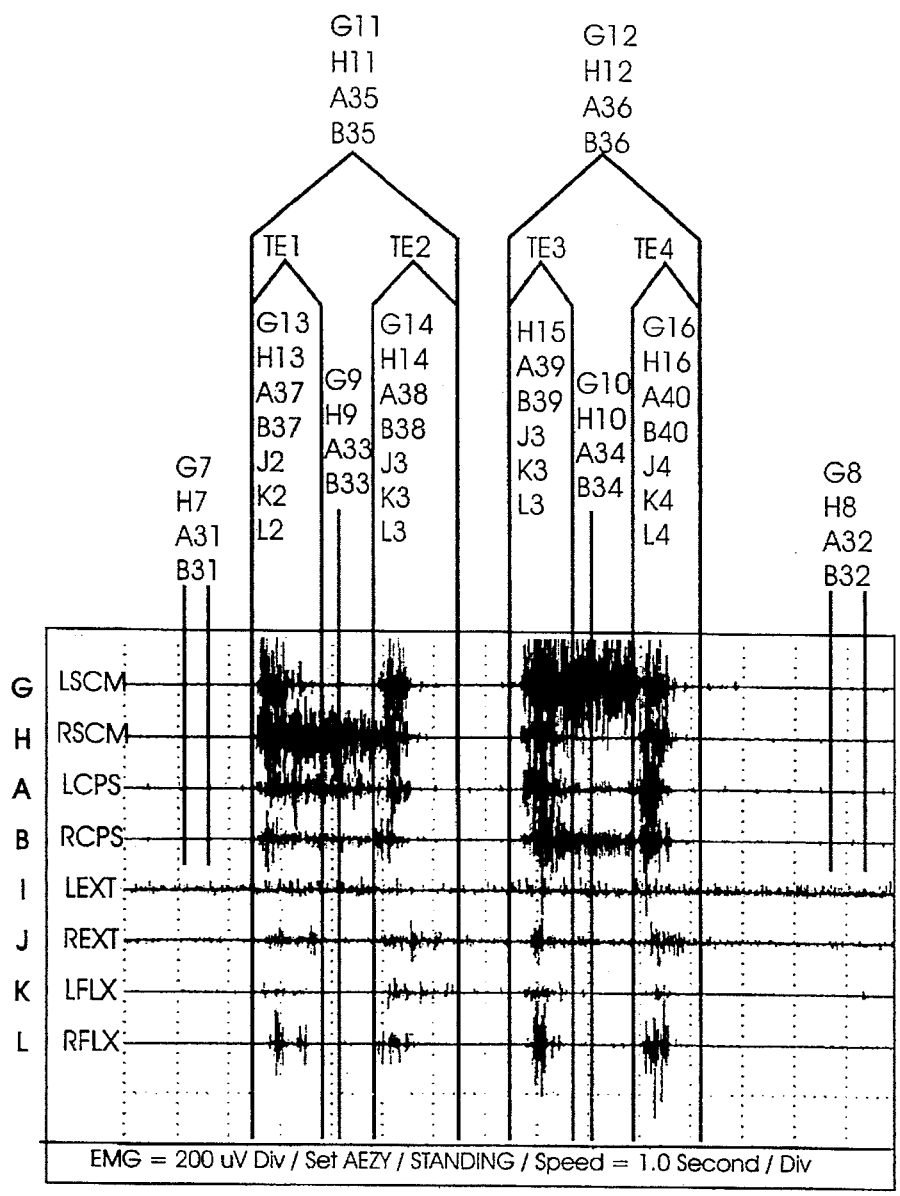
Fig. 3G Protocol 7

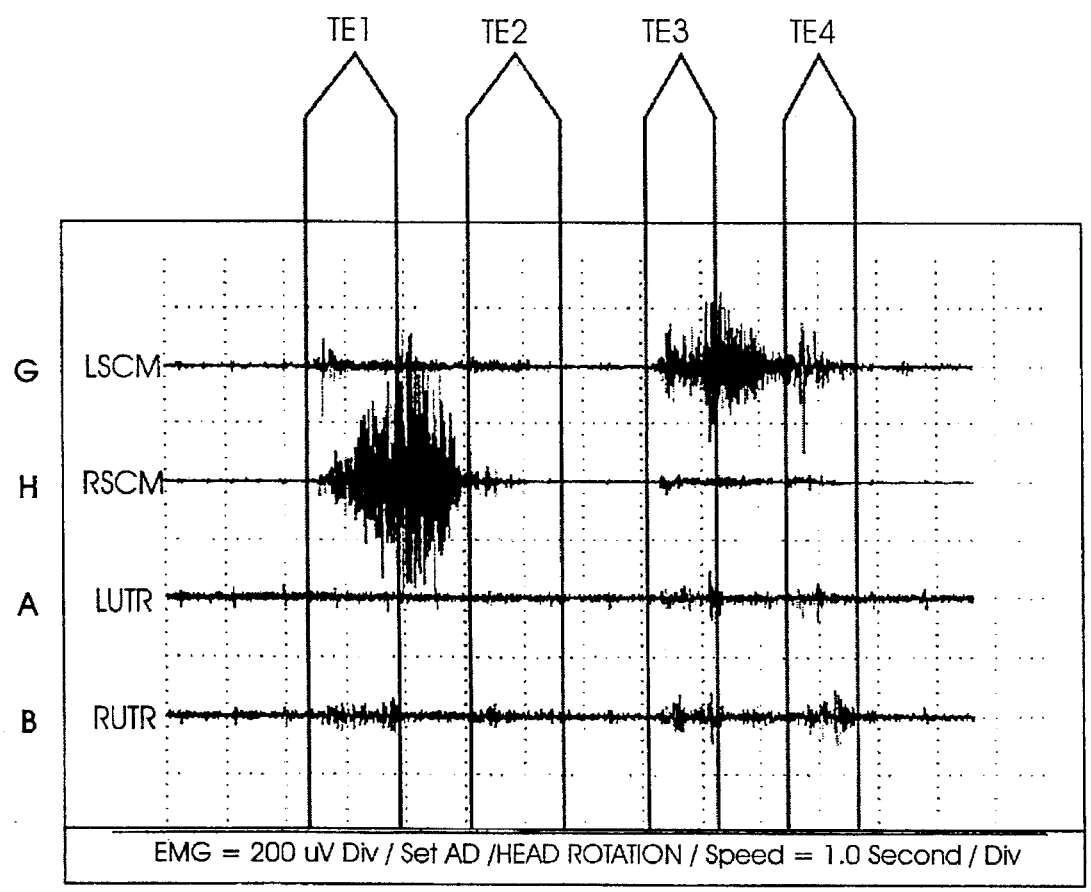
Fig. 3H Protocol 7

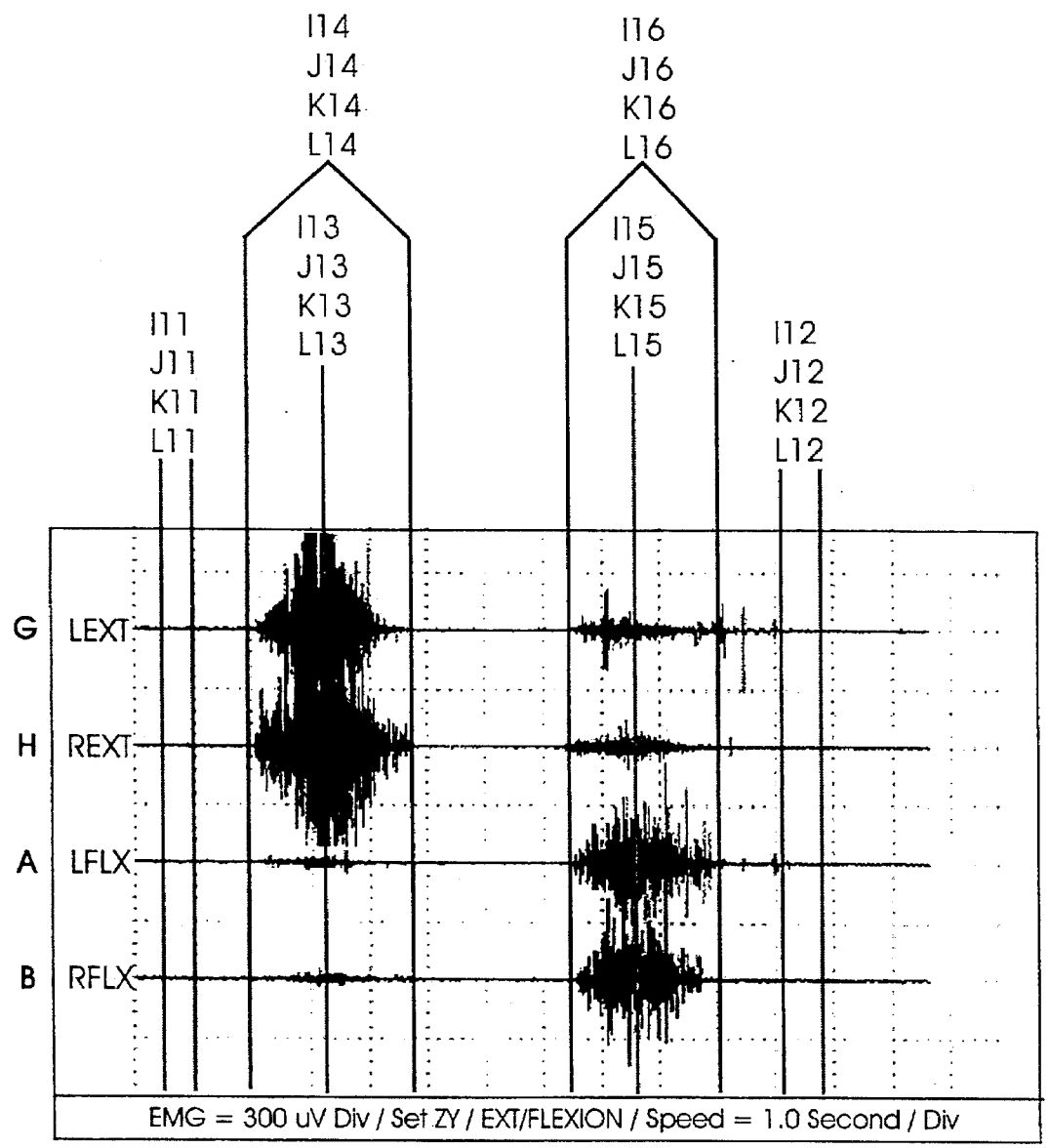
Fig. 31 Protocol 9

SYSTEM FOR DIAGNOSING MUSCULOSKELETAL DISORDERS

FIELD OF THE INVENTION

The present invention relates generally to methods and apparatus for diagnosing musculoskeletal disorders in the upper quarter of a human body.

BACKGROUND OF THE INVENTION

Musculoskeletal pain refers to pain arising from the muscles, ligaments, tendons and bones. Musculoskeletal pain is by far the most common type of pain experienced by patients, especially in the workplace. For example, the Bureau of Labor Statistics reported that in 1992, one million of the 2.3 million nonfatal occupational injuries and illnesses which resulted in days away from work involved musculoskeletal disorders. Of the one million injuries and illnesses, the Occupational Safety and Health Administration (OSHA) estimates that 280,000 involved cumulative trauma disorders of the upper extremities, such as wrists, shoulders or elbows. Such injuries make up the fastest growing, most widespread occupational hazard in the United States today. In fact, the problem has grown so acute that OSHA has proposed new sweeping occupational safety standards that would reach into virtually every workplace.

Notwithstanding the enormous prevalence of musculoskeletal disorders, the scientific study of muscle pain, per se, and musculoskeletal dysfunction, in general, has lagged far behind advances in other areas of medicine. One reason for this lag is that there is a lack of a clear understanding of the basic pathophysiology of pain arising from muscles. Another reason is the lack of scientific technology to obtain and document objective patient data. As a result, many or most patients who experience musculoskeletal pain do not have a specific diagnosis.

Janet Travell, M.D. has conducted extensive research on myofascial trigger points. Her research has provided much needed perspective on the underlying cause of muscle pain and musculoskeletal dysfunction, including the clinical pain syndromes arising from myofascial trigger points in each muscle of the body. Her research emphasized a perspective of primarily biomechanical stressors which produce such trigger points.

Despite the extensive research by Dr. Travell, the perspective of the research failed to appreciate and explore the importance of psychophysiologic factors in musculoskeletal pain. Additionally, the research was entirely clinical, without objective documentation.

Accordingly, there is still a need for methods which can diagnose muscular dysfunction in patients with musculoskeletal pain and which can diagnose which proportion of pain is from biomechanical dysfunction and which proportion is from psychophysiologic dysfunction. The present invention fills these needs by providing a system for collecting muscle activity samples while a patient undergoing selected protocols, creating mathematical indices from the samples and comparing the indices to normative values.

SUMMARY OF THE INVENTION

The present invention provides a method for identifying muscular abnormalities in the upper quarter and forearm of a human patient. In a first embodiment, the method comprising the steps of selecting at least one protocol from a series of protocols based on physiological information from the patient, collecting muscle activity samples from one or more muscles of the patient while the patient performs the selected protocol, defining at least one index from a selected group of the collected samples, calculating the index from the selected group of collected samples, and comparing the calculated index to a normative range of values for the index to determine whether the index calculated for the patient is abnormal.

Another embodiment of the invention provides a method for determining dysfunctional psychophysiological muscle patterns in a patient comprising the steps of collecting muscle activity samples from one or more muscles of the patient while the patient undergoes one or more protocols, defining at least one psychophysiological index from a selected group of the collected samples, calculating the psychophysiological index from the selected group of the collected samples, and comparing the calculated psychophysiological index to a normative range of values for the index to determine whether the index calculated from the patient is abnormal, thereby indicating a psychophysiological dysfunction in the patient.

Yet another embodiment of the invention provides a method for determining dysfunctional biomechanical muscle patterns in a patient comprising the steps of collecting muscle activity samples from one or more muscles while the patient undergoes one or more protocols, defining at least one biomechanical index from a selected group of the collected samples, calculating the biomechanical index from the selected group of the collected samples, and comparing the calculated biomechanical index to a normative range of values for the index to determine whether the index calculated from the patient is abnormal, thereby indicating a biomechanical dysfunction in the patient.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings:

FIGS. 3A through 3I show printer-plotter outputs of patient EMG signals for different protocols.

DETAILED DESCRIPTION OF PREFERRED EMBODIMENTS

Certain terminology is used herein for convenience only and is not to be taken as a limitation on the invention.

Figure 1:
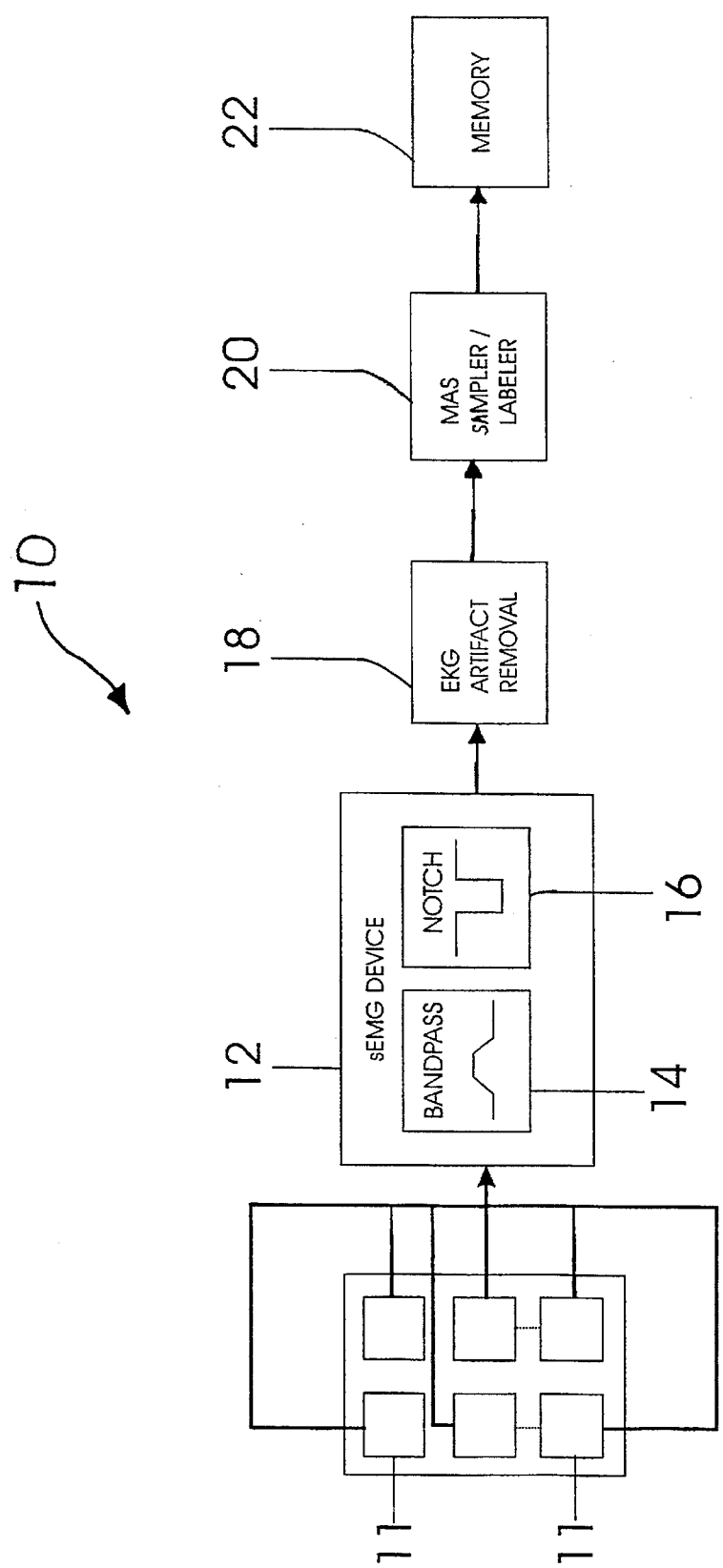
FIG. 1 is a schematic block diagram of a circuit according to a preferred embodiment of the present invention for collecting and processing patient electromyographic (EMG) signals.

Referring to the drawings, wherein the same reference numerals are employed for designating the same elements throughout the several figures, there is shown in FIG. 1 a preferred embodiment of a schematic block diagram of a system 10 for collecting EMG data. A plurality of electrodes 11 are connected to muscle locations on a patient (not shown) to be diagnosed. In one example of electrode placement, two silver/silver chloride 8 mm surface electrodes are placed parallel to the belly muscle, over the middle one-third of the muscle, and 3 cm center to center. A universal reference is placed over the supraspinous process of C7. Specific electrode placements are as follows:

1. Upper trapezius, 2 cm posterior to the medial attachment of the trapezius to the clavicle; left upper trapezius designated A, right upper trapezius designated B.
2. Lower trapezius, 2 cm medial to the inferior pole of the scapula; left lower trapezius designated C, right lower trapezius designated D.
3. Scalene muscle, 2 cm superior to the level of the clavicle; left-E, right-F.
4. Sternocleidomastoid, sternal division, 2 cm superior to the attachment of the sternum; left-G, right-H.
5. Extensor surface of the forearm, midpoint, predominantly over the extensor digitorum muscle; left-I, right-J.
6. Flexor surface of the forearm, midpoint, predominantly over the flexor digitorum superficialis muscle, left-K, right-L.

Four to eight channels of surface EMG (sEMG) data are simultaneously collected and recorded by sEMG device 12 over a period of 15–30 seconds from different muscles (the specific muscles varying according to the below described specific protocol). The sEMG device includes a 45–400 HZ bandpass filter 14, a notch filter 16 at 60 HZ, and a sampling rate greater than 50 samples/second. An EKG artifact removal circuit 18 removes superimposed EKG artifact(s) from the sEMG tracings prior to analysis. Muscle activity sampling and labeling circuit 20 samples muscle activity within specific time intervals and at specific times of the recording. The muscle activity samples (MAS) are labeled for each individual muscle (i.e., A1, A2, A3, . . . ) and stored in memory 22 for later analysis.

One sEMG device 12 which is suitable for use in practicing the present invention is Version 1.51, Flex Comp, manufactured by Thought Technology, LTD, 2180 Belgrave Ave., Montreal, Quebec, Canada, H4A2L8. The remaining circuit elements 18, 20 and 22 shown schematically in FIG. 1 are well-known in the art and, thus, are not further described. However, it will be appreciated by those skilled in the art that the present invention may be practiced by other devices or equipment and that the present invention is not limited to a particular device.

Figure 2:
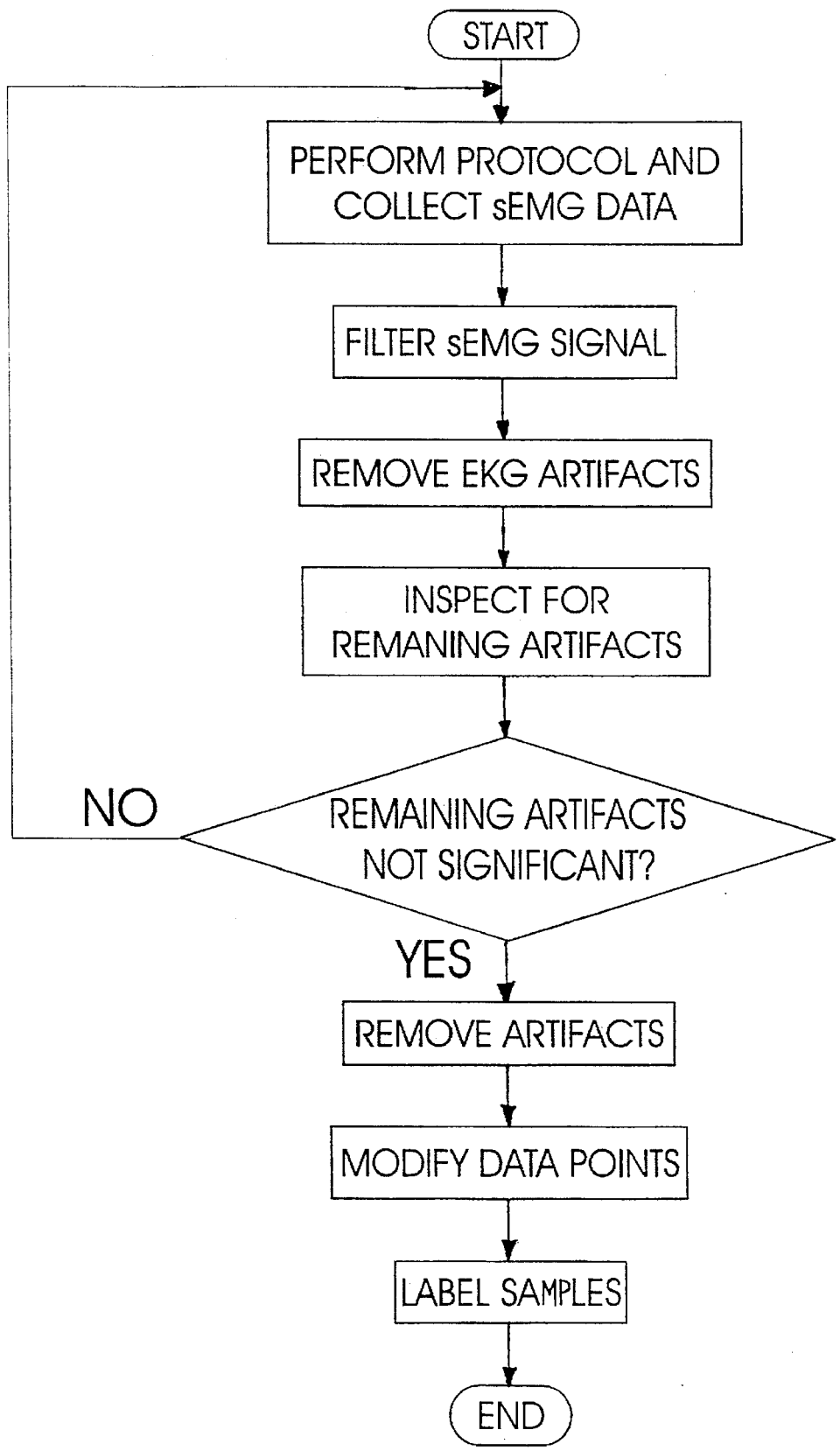
FIG. 2 is a flowchart illustrating the data collection process of the invention.

Individual tracings of sEMG are visually inspected by a trained operator for any artifacts at the time of data collection. If significant artifacts are present, the protocol is repeated. If none or only minor artifacts are present, data points are modified by ±1 second as to the time of the sample prior to MAS labeling by the circuit 20. The entire diagnostic protocol is performed without any exposure by the patient to any of the sEMG tracings. FIG. 2 is a flowchart showing the various steps of the data collection process described above.

In collecting the data, four different types of muscle activity samples (listed below) are collected, labeled and stored.

1. Data point (DP)—An averaged amplitude of sEMG activity in microvolts (μv) over 0.5 second time intervals. The exact location of the data point can vary by ±1 second if significant artifact is present. If so, all sEMG channels are varied identically.
2. Peak amplitude (PA)—the maximum amplitude in μv for a specified activity in a specified muscle. Artefact affecting the determination of peak amplitude is visually identified and eliminated.
3. Total muscle activity (TMA)—the total electrical activity in μv/second for a specified muscle for a specified time interval.
4. Time-linked muscle activity (TLMA)—bursts of muscle activity occurring at the onset/completion of head rotation movements, measured in μv/second, which occur simultaneously in two to eight of the muscles having their activity recorded, having a duration of less than 1.5 seconds and which are clearly distinguished from data attributed to background rotational movements and/or continuous background activity. All instances of TLMA are visually identified according to the above criteria. A single time epoch (TE) for each head rotation movement which contains all TLMA in each of the eight muscles recorded is visually identified. The single time epoch may vary among rotation movements. The total muscle activity (TMA) within each time epoch that is distinguishable from background rotational movements and/or continuous background activity is determined as the TLMA.

To summarize, there are four different types of muscle activity samples; data point samples, peak amplitude samples, total muscle activity samples and time linked muscle activity samples. Each sample is designated by a letter and number combination. The letter of each sample designates the particular muscle and muscle location with which the sample is associated. For example, A1, A2 . . . , An are all samples collected from the left upper trapezius. However, A1 is a data point sample, A7 is a peak amplitude sample, A8 is a total muscle activity sample, and A37 is a time linked muscle activity sample. The disclosed embodiment of the invention takes samples from twelve different muscle/muscle locations (A–L). The number of the sample corresponds to a particular protocol and a particular time frame during the protocol, as described below. Some muscles have a large number of samples because the muscles are employed in a many protocols and/or because the particular protocol requires collecting a large number of samples from the muscles. For example, a total of 50 samples are taken from the left upper trapezius (A), whereas only 12 samples are taken from the left lower trapezius (C). To better understand the overall data collection scheme, some examples of types of muscle activity samples and their designated letter-number combination are listed below:

1. data points (e.g., A1, B1)
2. peak amplitude (e.g., A7, B7)
3. total muscle activity (e.g., A8, B8)
4. time linked muscle activity (e.g., A37, B37)

Protocols are selected in accordance with the specific complaints described by the patient. Protocols 1–6 are utilized for patients with head, neck and shoulder complaints but with minimal or no arm/hand complaints. Such complaints are designated as primary upper quarter myofascial syndrome (PUQ). Protocols 1–5 and 7–9 are utilized for patients with arm/hand complaints, designated as upper quarter, upper extremity myofascial syndrome (UQUE). While the appropriate protocols are preferably selected based on physiological "complaints," it is within the scope of the invention to employ other forms of physiological information (e.g., other patient test data) to select the appropriate protocols.

Each protocol involves one or more muscles/muscle locations, designated by their respective letters. Each protocol is defined by a patient position, a plurality of maneuvers which the patient undergoes while in the position and a plurality of muscle activity samples collected during the protocol.

FIGS. 3A through 3I show graphical printer-plotter printout results of actual raw EMG data for each of the nine respective protocols from an actual patient. The following abbreviations in the printouts identify the muscles. The single letters (A–L) following the muscle description also designate the respective muscles in the protocols below:

LUTP—left upper trapezius (A)
RUTP—right upper trapezius (B)
LLTP—left lower trapezius (C)
RLTP—right lower trapezius (D)
LSCA—left scalene muscle (E)
RSCA—right scalene muscle (F)
LSCM—left sternocleidomastoid (G)
RSCM—right sternocleidomastoid (H)
LEXT—left extensor surface of the forearm (I)
REXT—right extensor surface of the forearm (J)
LFLX—left flexor surface of the forearm (K)
RFLX—right flexor surface of the forearm (L)

Protocol 1—Trapezius (A, B, C, D)

a. Patient position—sitting in chair, arms resting quietly in the lap.

b. Maneuver—2.5 seconds of sEMG activity is recorded without specific instruction to the patient. The patient is then instructed to shrug the shoulders (i.e., elevate the shoulders as high as possible) and hold for 3–4 seconds (the shrug procedure having been previously demonstrated to the patient). The patient is then instructed to relax the shoulders. sEMG activity is recorded during the shrug and the following 10 seconds of relaxation.

c. Muscle activity sampling.

1. Data points, A1, B1, C1, D1 are obtained 1 second prior to the onset of the shrug.
2. Data points, A2, B2, C2, D2 are obtained 2 seconds after completion of the shrug.

FIG. 3A shows raw EMG data from a particular patient who underwent Protocol 1. The data points are labeled at the respective time periods.

Protocol 2—Trapezius (A, B, C, D)

a. Patient position—standing, arms resting by the side.

b. Maneuver—identical to Protocol 1.

c. Muscle activity sampling.

1. Data points, A3, B3, C3, D3 are obtained 1 second prior to the onset of the shrug.
2. Data points, A4, B4, C4, D4 are obtained 2 seconds after completion of the shrug.

FIG. 3B shows raw EMG data from a particular patient who underwent Protocol 2. The data points are labeled at the respective time periods.

Protocol 3—Trapezius (A, B, C, D)

a. Patient position—sitting in chair, arms resting quietly in the lap.

b. Maneuver—2 seconds of sEMG activity is recorded without specific instruction. The patient is then instructed to abduct the arms 90 degrees (the abduction maneuver having been previously demonstrated by the examiner) and to hold this position for 3 seconds. The patient is then instructed to relax the arms to the sides, sEMG activity being recorded both during the abduction and the following 10 seconds of relaxation.

c. Muscle activity sampling.

1. Data points, A5, B5, C5, D5 are obtained 1 second prior to the onset of abduction.
2. Data points, A6, B6, C6, D6 are obtained 2 seconds after the completion of abduction.
3. Peak amplitudes, A7, B7, C7, D7 are obtained during the 3 seconds of the abduction maneuver.
4. Total muscle activities, A8, B8, C8, D8 are obtained during the 3 seconds of the abduction maneuver.

FIG. 3C shows raw EMG data from a particular patient who underwent Protocol 3. The data points and peak amplitudes are labeled at the respective time periods. The beginning and end times associated with the total muscle activity are also labeled.

Protocol 4—Trapezius (A, B, C, D)

a. Patient position—standing, arms resting by the side.

b. Maneuver—identical to Protocol 3.

c. Muscle activity sampling.

1. Data points, A9, B9, C9, D9 are obtained 1 second prior to the onset of abduction.
2. Data points, A10, B10, C10, D10 are obtained 2 seconds after the completion of abduction.
3. Peak amplitudes, A11, B11, C11, D11 are obtained during the 3 seconds of the abduction maneuver.
4. Total muscle activities, A12, B12, C12, D12 are obtained during the 3 seconds of the abduction maneuver.

Since Protocol 4 is identical to Protocol 3 (except for a different patient position), FIG. 3C serves as an illustration of typical raw EMG data for Protocol 4.

Protocol 5—Trapezius, Scalene (A, B, E, F)

a. Patient position—standing, arms resting by the side.

b. Maneuver—sEMG activity of 5 normal breath or respiratory cycles is recorded. The patient is then instructed to take 5 deep breaths with the mouth closed, (the maneuver having been previously been demonstrated to the patient by the examiner), sEMG activity being recorded during the 5 deep breaths. Since only the upper trapezius and scalene muscles are recorded during the respiratory cycle, only the muscle activity of inspiration is recorded.

c. Muscle activity sampling.

1. Data points, A13, B13, E1, F1 are obtained 1 second prior to the first normal inspiration.
2. Data points, A14, B14, E2, F2 are obtained 3 seconds after the fifth forced inspiration.
3. Peak amplitudes, A15–19, B15–19, E3–7, F3–7 are obtained during each of the five forced inspirations.
4. Total muscle activities, A20–24, B20–24, E8–12, F8–12 are obtained during each of the five forced inspirations.

FIGS. 3D and 3E show raw EMG data from a particular patient who underwent Protocol 5. FIG. 3D shows the five normal inspirations. FIG. 3E shows the five forced inspirations. The data points and peak amplitudes are labeled at the respective time periods. The beginning and end times associated with the total muscle activity are also labeled.

Protocol 6—Trapezius, Sternocleidomastoid (A, B, G, H)

a. Patient position—sitting in a chair, arms resting quietly in lap.

b. Maneuver—2 seconds of sEMG activity is recorded with the head in neutral position. The patient is then instructed to rotate the head as far to the left as is comfortably possible without pain, hold this position for 3 seconds and then return the head to the neutral position, holding this position for 2 seconds. The patient is then instructed to rotate the head as far to the right as is comfortably possible without pain, hold this position for 3 seconds and then return the head to the neutral position, (this entire maneuver having been previously demonstrated to the patient by the examiner). No attempt to control the speed of rotation is made.

c. Muscle activity sampling.
1. Data points, A25, B25, G1, H1 are obtained 1 second prior to the onset of head rotation to the left.
2. Data points, A26, B26, G2, H2 are obtained 2 seconds after return to the neutral position from head rotation right.
3. Peak amplitudes, A27, B27, G3, H3 are obtained during the 3 seconds of head rotation to the left; peak amplitudes, A28, B28, G4, H4 are obtained during the 3 seconds of head rotation to the right.
4. Total muscle activities, A29, B29, G5, H5 are obtained during the 3 seconds of head rotation to the left; total muscle activities, A30, B30, G6, H6 are obtained during the 3 seconds of head rotation to the right.

FIG. 3F shows raw EMG data from a particular patient who underwent Protocol 6. The data points and peak amplitudes are labeled at the respective time periods. The beginning and end times associated with the total muscle activity are also labeled.

Protocol 7—Trapezius, Sternocleidomastoid,
Extensors/Flexors of Forearm
(A, B, G, H, I, J, K, L)

a. Patient position—sitting in a chair, arms resting quietly in the lap.
b. Maneuver—2 seconds of sEMG is recorded with the head in neutral position. The patient is then instructed to rotate the head as far to the left as is comfortably possible without pain, hold this position for 3 seconds and then return the head to the neutral position, holding this position for 2 seconds. The patient is then instructed to rotate the head as far to the right as is comfortably possible without pain, hold this position for 3 seconds and then return the head to the neutral position, (this entire maneuver having been previously demonstrated to the patient by the examiner). No attempt to control the speed of rotation is made.
c. Muscle activity sampling.
1. Data points, A31, B31, G7, H7 are obtained 1 second prior to the onset of head rotation to the left.
2. Data points, A32, B32, G8, H8 are obtained 2 seconds after return to the neutral position from head rotation right.
3. Peak amplitudes, A33, B33, G9, H9 are obtained during the 3 seconds of head rotation to the left; peak amplitudes, A34, B34, G10, H10 are obtained during the 3 seconds of head rotation to the right.
4. Total muscle activities, A35, B35, G11, H11 are obtained during the 3 seconds of head rotation to the left; total muscle activities A36, B36, G12, H12 are obtained during the 3 seconds of head rotation to the right.
5. Total muscle activities, I1, J1, K1, L1 are obtained for the entire 15 seconds of the protocol.
6. Time-linked muscle activities, A37, B37, G13, H13, I2, J2, K2, L2 are obtained at the onset of head rotation to the left; time-linked muscle activities, A38, B38, G14, H14, I3, J3, K3, L3 are obtained at the completion of head rotation to the left; time-linked muscle activities, A39, B39, G15, H15, I4, J4, K4, L4 are obtained at the onset of head rotation to the right; time-linked muscle activities, A40, B40, G16, H16, I5, J5, K5, L5 are obtained at the completion of head rotation to the right.

FIG. 3G shows raw EMG data from a particular patient who underwent Protocol 7. The data points, peak amplitudes and the beginning and end times associated with the total muscle activity are labeled. The beginning and end times associated with each time epoch ($TE_1$–$TE_4$) containing time-linked muscle activity (TLMA) are also labeled.

TLMA are also labeled. TLMA does not occur in all eight channels of muscle activity in each time epoch. In FIG. 3G, only seven channels demonstrate TLMA in $TE_1$, the same seven channels demonstrate TLMA in $TE_2$, a different set of six channels demonstrate TLMA in $TE_3$, and the original seven channels demonstrate TLMA in $TE_4$.

For further clarity with respect to TLMA, FIG. 3H illustrates only TLMA in sternocleidomastoid and upper trapezius. The enlarged scale of tracings allows for better definition of TLMA in these muscles.

Protocol 8—Trapezius, Sternocleidomastoid,
Extensors/Flexors of forearm
(A, B, G, H, I, J, K, L)

a. Patient position—standing, arms resting quietly by the side.
b. Maneuver—identical to Protocol 6.
c. Muscle activity sampling.
1. Data points, A41, B41, G17, H17 are obtained 1 second prior to the onset of head rotation to the left.
2. Data points, A42, B42, G18, H18 are obtained 2 seconds after return to the neutral position from head rotation right.
3. Peak amplitudes, A43, B43, G19, H19 are obtained during the 3 seconds of head rotation to the left; peak amplitudes, A44, B44, G20, H20 are obtained during the 3 seconds of head rotation to the right.
4. Total muscle activities, A45, B45, G21, H21 are obtained during the 3 seconds of head rotation to the left; total muscle amplitudes A46, B46, G22, H22 are obtained during the 3 seconds of head rotation to the right.
5. Total muscle activities, I6, J6, K6, L6 are obtained for the entire 15 seconds of the protocol.
6. Time-linked muscle activities, A47, B47, G23, H23, I7, J7, K7, L7 are obtained at the onset of head rotation to the left; time-linked muscle activities, A48, B48, G24, H24, I8, J8, K8, L8 are obtained at the completion of head rotation left; time-linked muscle activities, A49, B49, G25, H25, I9, J9, K9, L9 are obtained at the onset of head rotation right; time-linked muscle activities, A50, B50, G26, H26, I10, J10, K10, L10 are obtained at the completion of head rotation right.

Since Protocol 8 is identical to Protocol 7, except for the patient position, FIGS. 3G and 3H serve as an illustration of the type of raw EMG data expected during Protocol 8.

Protocol 9—Extensors/Flexors of
Forearm (I, J, K, L)

a. Patient position—standing, arms resting quietly by the side.
b. Maneuver—2 seconds of sEMG is recorded without specific instruction. The patient is then instructed to extend the wrists as far as is comfortably possible without pain, hold this position for 3 seconds and then return to the neutral position, holding this position for 3 seconds. The patient is then instructed to flex the wrists as far as is comfortably possible without pain, hold this position for 3 seconds and then return to the neutral position, (this entire maneuver having been previously demonstrated to the patient by the examiner).
c. Muscle activity sampling.
1. Data points, I11, J11, K11, L11 are obtained 1 second prior to the onset of wrist extension.
2. Data points, I12, J12, K12 L12 are obtained 2 seconds after the completion of wrist flexion.
3. Peak amplitudes, I13, J13, K13, L13 are obtained during the 3 second of wrist extension; peak amplitudes I14, J14, K14, L14 are obtained during the 3 seconds of wrist flexion.

4. Total muscle activities, I15, J15, K15, L15 are obtained during the 3 seconds of wrist extension; total muscle activities I16, J16, K16, L16 are obtained during the 3 seconds of wrist flexion.

FIG. 3I shows raw EMG data from a particular patient who underwent Protocol 9. The data points and peak amplitudes are labeled at the respective time periods. The beginning and end times associated with the total muscle activity are also labeled.

Once all of the samples of all of the applicable protocols are collected, selected groups or groupings of muscle activity samples are algebraically combined to define different indices. In the present embodiment, there are four psychophysiologic indices and two biomechanical indices associated with the primary upper quarter myofascial syndrome. There are also four psychophysiologic indices and two biomechanical indices associated with the upper quarter, upper extremity myofascial syndrome. In addition, there is a forearm index associated with the upper quarter, upper extremity myofascial syndrome. Some of the psychophysiologic indices include sub-indices for each of the muscles. The indices and sub-indices are algebraically created as follows:

A. Primary Upper Quarter Myofascial Syndrome (PUQ)

1. Psychophysiologic Index I (PI1)
a. Trapezius
  1. $A1+A2+A3+A4+A5+A6+A9+A10+A13+A14+A25+A26=\text{APUQ}_{PI1}$
  2. $B1+B2+B3+B4+B5+B6+B9+B10+B13+B14+B25+B26=\text{BPUQ}_{PI1}$
  3. Trapezius $\text{PUQ}_{PI1}=\text{APUQ}_{PI1}+\text{BPUQ}_{PI1}$
b. Scalene
  1. $E1+E2=\text{EPUQ}_{PI1}$
  2. $F1+F2=\text{FPUQ}_{PI1}$
  3. Scalene $\text{PUQ}_{PI1}=\text{EPUQ}_{PI1}+\text{FPUQ}_{PI1}$
c. Sternocleidomastoid (SCM)
  1. $G1+G2=\text{GPUQ}_{PI1}$
  2. $H1+H2=\text{HPUQ}_{PI1}$
  3. SCM $\text{PUQ}_{PI1}=\text{GPUQ}_{PI1}+\text{HPUQ}_{PI1}$
d. Total upper quarter $\text{PI1}=\text{APUQ}_{PI1}+\text{BPUQ}_{PI1}+\text{EPUQ}_{PI1}+\text{FPUQ}_{PI1}+\text{GPUQ}_{PI1}+\text{HPUQ}_{PI1}$ 2. Psychophysiologic Index II (PI2)
a. Trapezius
  1. $(A6-A5)+(A10-A9)=\text{APUQ}_{PI2}$
  2. $(B6-B5)+(B10-B9)=\text{BPUQ}_{PI2}$
  3. Trapezius $\text{PUQ}_{PI2}=\text{APUQ}_{PI2}+\text{BPUQ}_{PI2}$
b. Scalene
  1. Scalene $\text{PUQ}_{PI2}=(E2-E1)+(F2-F1)$ 3. Psychophysiologic Index III (PI3)
a. Trapezius
  1. $(A2-A1)+(A4-A3)=\text{APUQ}_{PI3}$
  2. $(B2-B1)+(B4-B3)=\text{BPUQ}_{PI3}$
  3. Trapezius $\text{PUQ}_{PI3}=\text{APUQ}_{PI3}+\text{BPUQ}_{PI3}$ 4. Psychophysiologic Index IV (PI4–5)
a. Trapezius
  1. $(A7/C7)+(A11/C11)=\text{Left PUQ}_{PI4}$
  2. $(B7/D7)+(B11/D11)=\text{Right PUQ}_{PI4}$
  3. $(A8/C8)+(A12/C12)=\text{Left PUQ}_{PI5}$
  4. $(B8/D8)+(B12/D12)=\text{Right PUQ}_{PI5}$
  5. Trapezius $\text{PUQ}_{PI4-5}=\text{Left PUQ}_{PI4}+\text{Right PUQ}_{PI4}+\text{Left PUQ}_{PI5}+\text{Right PUQ}_{PI5}$ 5. Biomechanical Index I (BI1)
a. Trapezius
  1. $(A7-B7)+(A11-B11)+(A15-B15)+(A16-B16)+(A17-B17)+(A18-B18)+(A19-B19)+(A27-B27)+(A28-B28)=\text{Trapezius PUQ}_{BI1}$
  2. $\text{APUQ}_{PI1}-\text{BPUQ}_{PI1}=\text{Trapezius PUQ}_{PI1BI1}$
  3. Total Trapezius $\text{PUQ}_{BI1}=\text{Trapezius PUQ}_{BI1}+\text{Trapezius PUQ}_{PI1-BI1}$
b. Scalene (BI1)
  1. $(E3-F3)+(E4-F4)+(E5-F5)+(E6-F6)+(E7-F7)=\text{Scalene PUQ}_{BI1}$
  2. $\text{EPUQ}_{PI1}-\text{FPUQ}_{PI1}=\text{Scalene PUQ}_{PI1-BI1}$
  3. Total Scalene $\text{PUQ}_{BI1}=\text{Scalene PUQ}_{BI1}+\text{Scalene PUQ}_{PI1-BI1}$
c. Sternocleidomastoid (SCM)
  1. $(G3-H3)+(G4-H4)=\text{SCM PUQ}_{BI1}$
  2. $\text{GPUQ}_{PI1}-\text{HPUQ}_{PI1}=\text{SCM PUQ}_{PI1-BI1}$
  3. Total SCM $\text{PUQ}_{BI1}=\text{SCM PUQ}_{BI1}+\text{SCM PUQ}_{PI1-BI1}$
d. Total upper quarter $\text{PUQ}_{BI1}=\text{Total Trapezius PUQ}_{BI1}+\text{Total Scalene PUQ}_{BI1}+\text{Total SCM PUQ}_{BI1}$ 6. Biomechanical Index II (BI2)
a. Trapezius
  1. $(A8-B8)+(A12-B12)+(A20-B20)+(A21-B21)+(A22-B22)+(A23-B23)+(A24-B24)+(A29-B29)+(A30-B30)=\text{Trapezius PUQ}_{BI2}$
  2. $\text{APUQ}_{PI2}-\text{BPUQ}_{PI2}=\text{Trapezius PUQ}_{PI2-BI2}$
  3. Total Trapezius $\text{PUQ}_{BI2}=\text{Trapezius PUQ}_{BI2}+\text{Trapezius PUQ}_{PI2-BI2}$
b. Scalene
  1. $(E8-F8)+(E9-F9)+(E10-F10)+(E11-F11)+(E12-F12)=\text{Scalene PUQ}_{BI2}$
  2. $\text{EPUQ}_{PI2}-\text{FPUQ}_{PI2}=\text{Scalene PUQ}_{PI2-BI2}$
  3. Total Scalene $\text{PUQ}_{BI2}=\text{Scalene PUQ}_{BI2}+\text{Scalene PUQ}_{PI2-BI2}$
c. Sternocleidomastoid (SCM)
  1. $(G5-H5)+(G6-H6)=\text{SCM PUQ}_{BI2}$
  2. $\text{GPUQ}_{PI2}-\text{HPUQ}_{PI2}=\text{SCM PUQ}_{PI2-BI2}$
  3. Total SCM $\text{PUQ}_{BI2}=\text{SCM PUQ}_{BI2}+\text{SCM PUQ}_{PI2-BI2}$
d. Total upper quarter $\text{PUQ}_{BI2}=\text{Total Trapezius PUQ}_{BI2}+\text{Total Scalene PUQ}_{BI2}+\text{Total SCM PUQ}_{BI2}$

B. Upper Quarter, Upper Extremity Myofascial Syndrome (UQUE)

1. Psychophysiologic Index PIuque 1-5 is identical to PIpuq 1-5 as described above.

2. Biomechanical Index BIuque 1-2 is identical to BIpuq 1-2 as described above.

3. Forearm Index
a. Time-linked activity for the neck (TLAN).
  1. $G13+G14+G15+G16+G23+G24+G25+G26=\text{GUQUE}_{TLANFI}$
  2. $F13+F14+F15+F16+F23+F24+F25+F26=\text{FUQUE}_{TLANFI}$
  3. $A37+A38+A39+A40+A47+A48+A49+A50=\text{AUQUE}_{TLANFI}$
  4. $B37+B38+B39+B40+B47+B48+B49+B50=\text{BUQUE}_{TLANFI}$
  5. Neck $\text{UQUE}_{TLANFI}=\text{GUQUE}_{TLANFI}+\text{FUQUE}_{TLANFI}+\text{AUQUE}_{TLANFI}+\text{BUQUE}_{TLANFI}$
b. Time-linked activity for the forearm (TLAF)
  1. $I2+I3+I4+I5+I7+I8+I9+I10=\text{IUQUE}_{TLAFFI}$
  2. $J2+J3+J4+J5+J7+J8+J9+J10=\text{JUQUE}_{TLAFFI}$ 3. $K2+K3+K4+K5+K7+K8+K9+K10=\text{KUQUE}_{TLAFFI}$ 4. $L2+L3+L4+L5+L7+L8+L9+L10=\text{LUQUE}_{TLAFFI}$ 5. Forearm $\text{UQUE}_{TLAFFI}=\text{IUQUE}_{TLAFFI}+\text{JUQUE}_{TLAFFI}+\text{KUQUE}_{TLAFFI}+\text{LUQUE}_{TLAFFI}$ c. Continuous activity (CA)

1. $I1+I6=\text{IUQUE}_{CAFI}$
2. $J1+J6=\text{JUQUE}_{CAFI}$
3. $K1+K6=\text{KUQUE}_{CAFI}$
4. $L1+L6=\text{LUQUE}_{CAFI}$
5. Forearm $\text{UQUE}_{CAFI}=\text{IUQUE}_{CAFI}+\text{JUQUE}_{CAFI}+\text{KUQUE}_{CAFI}+\text{LUQUE}_{CAFI}$ d. Combined forearm index (CFI)

1. $I1+I2+I3+I4+I5+I6+I7+I8+I9+I10=\text{IUQUE}_{CFI}$
2. $J1+J2+J3+J4+j5+J6+J7+J8+J9+J10=\text{JUQUE}_{CFI}$
3. $K1+K2+K3+K4+K5+K6+K7+K8+K9+K10=\text{KUQUE}_{CFI}$
4. $L1+L2+L3+L4+L5+L6+L7+L8+L9+L10=\text{LUQUE}_{CFI}$
5. Forearm $\text{UQUE}_{CFI}=\text{IUQUE}_{CFI}+\text{JUQUE}_{CFI}+\text{KUQUE}_{CFI}+\text{LUQUE}_{CFI}$ The relevant indices above are calculated for the patient and compared to a normative range of values. The normative range of values is determined by testing a population of healthy subjects who are not experiencing musculoskeletal pain. A database of normative values is established which is sufficiently large so that a patient can be matched with a subset of pain-free healthy patients having similar physiological characteristics (e.g., age, left/right-handness, sex, occupation and the like) which are known to affect EMG data.

Experimentation to date has yielded the following results:

1. A pain-free normative database of approximately 100 college students was collected. The students also underwent psychological testing to determine their levels of anxiety/mental tension. A direct relationship between anxiety/mental tension as determined from the psychological testing and the psychophysiological indices was observed. The biomechanical indices were generally low in this pain-free population.

2. Trials were conducted with patients complaining of pain. The psychophysiological and biomechanical indices correlated with the level of pain experienced by the patients. Specifically, the indices decreased as the pain decreased. Thus, a patient who is experiencing true muscular abnormalities will have higher indices than the pain-free population. If the patient has low levels of anxiety/mental tension (as determined by the psychological testing), high psychophysiological indices are even more likely to correlate with true muscular abnormalities since high indices resulting from anxiety or mental tension can be ruled out.

Experimentation performed to date suggests a continuum of musculoskeletal dysfunction from both a psychophysiological perspective and a biomechanical perspective, as opposed to a bimodal distribution of normals and abnormals. Experimentation performed to date also suggests that clinical pain typically appears in the setting of a combined psychophysiological and biomechanical dysfunction.

From the foregoing, it can be seen that the present invention comprises a system for scientifically diagnosing musculoskeletal disorders in the upper quarter of a human body and determining whether the pain is associated with a primary biomechanical dysfunction and/or a primary psychophysiologic dysfunction, or both. By recognizing the true origin of such pain, the medical community will be better able to more effectively treat patients who experience such pain.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A method for identifying muscular abnormalities of a human patient, the method comprising the steps of:
   (a) selecting at least one protocol from a series of protocols based on physiological information from the patient;
   (b) collecting muscle activity samples from one or more muscles of the patient while the patient performs the selected protocol;
   (c) defining at least one index from a selected group of the collected samples by algebraically combining a plurality of specified muscle activity samples or by algebraically combining a plurality of ratios of specified muscle activity samples;
   (d) calculating the index from the selected group of collected samples; and
   (e) comparing the calculated index to a normative range of values for the index to determine whether the index calculated for the patient is abnormal.

2. A method according to claim 1 wherein the protocol performed in step (b) includes:
   (i) placing the patient in a defined position,
   (ii) instructing the patient to undergo one or more maneuvers while in the position, and
   (iii) collecting a plurality of muscle activity samples as the patient undergoes the maneuvers.

3. The method according to claim 2 wherein the muscular abnormalities to be identified are in the upper quarter and forearm of the patient.

4. A method according to claim 3 wherein step (b) (i) includes having the patient sit, arms resting in the lap,
   the maneuvers performed in step (b) (ii) include a first non-specific instruction period followed by a shoulder shrug period and a shoulder relaxation period, and
   step (b) (iii) includes collecting a first set of data points from the upper and lower trapezius during the first period, and a second set of data points from the upper and lower trapezius during the shoulder relaxation period.

5. A method according to claim 3 wherein step (b) (i) includes having the patient stand, arms resting by the side,
   the maneuvers performed in step (b) (ii) include a first non-specific instruction period followed by a shoulder shrug period and a shoulder relaxation period, and
   step (b) (iii) includes collecting a first set of data points from the upper and lower trapezius during the first period, and a second set of data points from the upper and lower trapezius during the relaxation period.

6. A method according to claim 3 wherein step (b) (i) includes having the patient sit in a chair, arms resting in the lap,
   the maneuvers performed in step (b) (ii) include, sequentially, a first non-specific instruction period, an abduction maneuver and an arm relaxation period, and
   step (b) (iii) includes collecting a first set of data points from the upper and lower trapezius during the first period, a second set of data points from the upper and lower trapezius after completion of the abduction maneuver, a set of peak amplitudes from the upper and lower trapezius during the abduction maneuver, and a set of total muscle activity values from the upper and lower trapezius during the abduction maneuver.

7. A method according to claim 3 wherein step (b) (i) includes having the patient stand, arms resting by the side,
the maneuvers performed in step (b) (ii) include, sequentially, a first non-specific instruction period, an abduction maneuver and an arm relaxation period, and
step (b) (iii) includes collecting a first set of data points from the upper and lower trapezius during the first period, a second set of data points from the upper and lower trapezius after completion of the abduction maneuver, a set of peak amplitudes from the upper and lower trapezius during the abduction maneuver, and a set of total muscle activity values from the upper and lower trapezius during the abduction maneuver.

8. A method according to claim 3 wherein step (b) (i) includes having the patient stand, arms resting by the side,
the maneuvers performed in step (b) (ii) include a first period of normal respiration followed by a plurality of deep inspirations with the mouth closed, and
step (b) (iii) includes collecting a first set of data points from the upper trapezius and scalene muscle prior to the first period, a second set of data points from the upper trapezius and scalene muscle after completion of the plurality of deep inspirations, a set of peak amplitudes from the upper trapezius and scalene muscle during each of the plurality of deep inspirations, and a set of total muscle activity values from the upper trapezius and scalene muscle during each of the plurality of deep inspirations.

9. A method according to claim 3 wherein step (b) (i) includes having the patient sit, arms resting in the lap,
the maneuvers performed in step (b) (ii) include, sequentially, a first period of time where the head is in a neutral position, a rotation of the head as far to one side as is possible without experiencing pain, a holding of the head position for a second period of time followed by a return of the head to the neutral position, a rotation of the head as far to the other side as is possible without experiencing pain, a holding of the head position for a third period of time followed by a return of the head to the neutral position, and
step (b) (iii) includes collecting a first set of data points from the upper trapezius and sternocleidomastoid during the first period and shortly prior to the first head rotation, a second set of data points from the upper trapezius and sternocleidomastoid after completion of the second head rotation, a set of peak amplitudes from the upper trapezius and sternocleidomastoid during each of the head rotations, and a set of total muscle activity values from the upper trapezius and sternocleidomastoid during each of the head rotations.

10. A method according to claim 3 wherein step (b) (i) includes having the patient sit, arms resting in the lap,
the maneuvers performed in step (b) (ii) include, sequentially, a first period of time where the head is in a neutral position, a rotation of the head as far to one side as is comfortably possible without experiencing pain, a holding of the head in the maximally rotated position for a second period of time followed by a return of the head to the neutral position, a rotation of the head as far to the other side as is comfortably possible without experiencing pain, a holding of the head in the maximally rotated position for a third period of time followed by a return of the head to the neutral position, and
step (b) (iii) includes collecting a first set of data points from the upper trapezius and sternocleidomastoid during the first period and shortly prior to the first head rotation, a second set of data points from the upper trapezius and sternocleidomastoid after completion of the second head rotation, a set of peak amplitudes from the upper trapezius and sternocleidomastoid during each of the head rotations, a set of total muscle activity values from the upper trapezius and sternocleidomastoid during each of the head rotations, a set of total muscle activity values from the extensor and flexor surfaces of the forearm, and a set of time-linked muscle activity values from the upper trapezius, sternocleidomastoid and extensor and flexor surfaces of the forearm at the onset and completion of each of the head rotations.

11. A method according to claim 3 wherein step (b) (i) includes having the patient stand, arms resting by the side,
the maneuvers performed in step (b) (ii) include, sequentially, a first period of time where the head is in a neutral position, a rotation of the head as far to one side as is comfortably possible without experiencing pain, a holding of the head in the maximally rotated position for a second period of time followed by a return of the head to the neutral position, a rotation of the head as far to the other side as is comfortably possible without experiencing pain, a holding of the head in the maximally rotated position for a third period of time followed by a return of the head to the neutral position, and
step (b) (iii) includes collecting a first set of data points from the upper trapezius and sternocleidomastoid during the first period and shortly prior to the first head rotation, a second set of data points from the upper trapezius and sternocleidomastoid after completion of the second head rotation, a set of peak amplitudes from the upper trapezius and sternocleidomastoid during each of the head rotations, a set of total muscle activity values from the upper trapezius and sternocleidomastoid during each of the head rotations, a set of total muscle activity values from the extensor and flexor surfaces of the forearm, and a set of time-linked muscle activity values from the upper trapezius, sternocleidomastoid and extensor and flexor surfaces of the forearm at the onset and completion of each of the head rotations.

12. A method according to claim 3 wherein step (b) (i) includes having the patient stand, arms resting by the side,
the maneuvers performed in step (b) (ii) include, sequentially, a first non-specific instruction time period where the wrist is in a neutral position, an extension of the wrist as far as is comfortably possible without experiencing pain, a holding of the wrist in the maximally extended position for a second period of time followed by a return of the wrist to the neutral position, a second period of time where the wrist is held in the neutral position, a flexing of the wrist as far as is comfortably possible without experiencing pain, and holding of the wrist position for a third period of time in the maximally flexed position followed by a return of the wrist to the neutral position, and
step (b) (iii) include collecting a first set of data points from the extensor and flexor surfaces of the forearm during the first period and shortly prior to the wrist extension, a second set of data points from the extensor and flexor surfaces after completion of the wrist flexion, a set of peak amplitudes from the extensor and flexor surfaces during the wrist extension and flexion, and a set of total muscle activity values from the extensor and flexor surfaces during the wrist extension and flexion.

13. A method according to claim 3 wherein the index is selected from the group comprising a psychophysiological index, a biomechanical index and a forearm index.

14. A method according to claim 3 wherein the index is related to a muscle selected from the group comprising the trapezius, scalene, sternocleidomastoid, extensor digitorum and flexor digitorum superficialis.

15. A method according to claim 1 wherein step (b) comprises collecting samples from a plurality of muscles, and the index is defined by the plurality of muscles.

16. A method according to claim 15 wherein the muscles are selected from the group comprising the trapezius, scalene, sternocleidomastoid, extensor digitorum and flexor digitorum superficialis.

17. A method according to claim 1 wherein the protocol performed in step (b) includes a plurality of patient actions selected from the group consisting of non-specific instruction periods, deliberate movements, relaxation periods and rest periods.

18. A method for determining dysfunctional psychophysiological muscle patterns in a patient comprising the steps of:
 (a) collecting muscle activity samples from one or more muscles of the patient while the patient undergoes one or more protocols;
 (b) defining at least one psychophysiological index from a selected group of the collected samples by algebraically combining a plurality of specified muscle activity samples or by algebraically combining a plurality of ratios of specified muscle activity samples;
 (c) calculating the psychophysiological index from the selected group of the collected samples; and
 (d) comparing the calculated psychophysiological index to a normative range of values for the index to determine whether the index calculated from the patient is abnormal, thereby indicating a psychophysiological dysfunction in the patient.

19. A method according to claim 18 wherein the protocol in step (a) includes performing a plurality of patient actions including movements, relaxation periods and rest periods.

20. A method according to claim 18 wherein the muscle activity samples are selected from the group comprising data points, peak amplitudes, total muscle activity and time linked muscle activity.

21. A method according to claim 18 wherein step (a) comprises collecting the samples with a multichannel surface electromyography device.

22. A method for determining dysfunctional biomechanical muscle patterns in a patient comprising the steps of:
 (a) collecting muscle activity samples from one or more muscles while the patient undergoes one or more protocols;
 (b) defining at least one biomechanical index from a selected group of the collected samples by algebraically combining a plurality of specified muscle activity samples;
 (c) calculating the biomechanical index from the selected group of the collected samples; and
 (d) comparing the calculated biomechanical index to a normative range of values for the index to determine whether the index calculated from the patient is abnormal, thereby indicating a biomechanical dysfunction in the patient.

\* \* \* \* \*